(12) United States Patent
Stadler (10) Patent No.: US 6,567,691 B1
(45) Date of Patent: May 20, 2003

(54) METHOD AND APPARATUS DIAGNOSIS AND TREATMENT OF ARRHYTHIAS (75) Inventor: Robert W. Stadler, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/532,478

(22) Filed: Mar. 22, 2000

(51) Int. Cl.[7] .......................... A61B 5/0468; A61N 1/39
(52) U.S. Cl. ............................................. 600/515; 607/4
(58) Field of Search .................. 607/5, 14, 4; 600/515, 600/518, 509, 510

(56) References Cited

U.S. PATENT DOCUMENTS

| | | |
|---|---|---|
| 4,146,029 A | 3/1979 | Ellinwood, Jr. |
| 4,316,472 A | 2/1982 | Mirowski et al. |
| 4,375,817 A | 3/1983 | Engle et al. |
| 4,384,585 A | 5/1983 | Zipes |
| 4,577,633 A | 3/1986 | Berkovits et al. |
| 4,587,970 A | 5/1986 | Holley et al. |
| 4,726,380 A | 2/1988 | Vollmann et al. |
| 4,727,877 A | 3/1988 | Kallok |
| 4,800,883 A | 1/1989 | Winstrom |
| 4,880,005 A | 11/1989 | Pless et al. |
| 4,949,719 A | 8/1990 | Pless et al. |
| 4,953,551 A | 9/1990 | Mehra et al. |
| 5,048,521 A | 9/1991 | Pless et al. |
| 5,058,599 A | 10/1991 | Andersen |
| 5,086,772 A | 2/1992 | Larnard et al. |
| 5,144,949 A | 9/1992 | Olson |
| 5,161,527 A | 11/1992 | Nappholz et al. |
| 5,163,427 A | 11/1992 | Keimel |
| 5,188,105 A | 2/1993 | Keimel |
| 5,193,535 A | 3/1993 | Bardey et al. |
| 5,193,550 A | 3/1993 | Duffin |
| 5,205,283 A | 4/1993 | Olson |
| 5,217,021 A | 6/1993 | Steinhaus et al. |
| 5,220,917 A | 6/1993 | Cammilli et al. |
| 5,282,465 A | 2/1994 | vanderVeen et al. |
| 5,312,441 A | 5/1994 | Mader et al. |
| 5,342,402 A | 8/1994 | Olson et al. |
| 5,527,344 A | 6/1996 | Arzbaecher et al. |
| 5,545,186 A | 8/1996 | Olson et al. |
| 5,549,649 A | 8/1996 | Florio et al. |
| 4,880,005 A | 10/1996 | Pless et al. |
| 5,755,736 A | 5/1998 | Gillberg et al. |
| 5,792,200 A | 8/1998 | Brewer |

FOREIGN PATENT DOCUMENTS

WO        9218198        10/1992

*Primary Examiner*—Scott M. Getzow
(74) *Attorney, Agent, or Firm*—Girma Wolde-Michael (57) ABSTRACT

Adaptive rules for a more accurate sinus tachycardia detection mechanism for implantable device (IMD) and other devices. In an embodiment, the rule is incorporated into a prioritized, rule-based arrhythmia classification system in an IMD. If the rule is met, anti-tachyarrhythmia therapy is withheld even if a lower priority rule determines presence of a treatable tachyarrhythmia. The rule includes adaptive onset criterion, where an expected range of R—R is calculated based on a trimmed mean and a metric of R—R variability derived over a preceding series of R—R intervals. Pattern codes indicative of gradual rate changes and normal sinus rhythm will be within a grammar defined by a continuous recognition machine and will if they persist, result in the ST rule being met. All other codes inconsistent with sinus tachycardia will not adhere to the associatd grammar and will result in the ST rule not being met.

50 Claims, 5 Drawing Sheets

| PRIOR R EVENT ST BEAT CODE: | CURRENT R EVENT ST BEAT CODE: | | | | | |
|---|---|---|---|---|---|---|
| | 0 | 1 | 2 | 3 | 4 | 5 |
| 0 | E | C | E | E | C | E |
| 1 | D | A | B | B | A | D |
| 2 | E | C | E | E | C | D |
| 3 | E | C | E | E | C | D |
| 4 | D | A | B | B | A | D |
| 5 | E | C | E | E | C | E |

FIG. 5

| ST PATTERN CODE: | CURRENT STATE: | | | | |
|---|---|---|---|---|---|
| | 0 [RESET] | 5 [A] | 10 [B] | 15 [C] | 20 [D] |
| A | - | 5 | - | 5 | - |
| B | - | 10 | - | 0 | - |
| C | 15 | - | 15 | - | 15 |
| D | 20 | 20 | 20 | 0 | - |
| E | 0 | - | 0 | - | 0 |

FIG. 6

METHOD AND APPARATUS DIAGNOSIS AND TREATMENT OF ARRHYTHIAS

BACKGROUND OF THE INVENTION

This invention relates to devices which detect and/or treat tachyarrhythmias (rapid heart rhythms), and more specifically, to mechanisms to distinguish among various tachyarrhythmias and to provide appropriate therapies to treat the identified tachyarrhythmias.

Early automatic tachyarrhythmia detection systems for automatic cardioverter/defibrillators relied upon the presence or absence of electrical and mechanical heart activity (such as intra-myocardial pressure, blood pressure, impedance, stroke volume or heart movement) and/or the rate of the electrocardiogram to detect hemodynamically compromising ventricular tachycardia or fibrillation.

In some pacemaker/cardioverter/defibrillators presently in commercial distribution or clinical evaluation, fibrillation is generally distinguished from ventricular tachycardia using ventricular rate based criteria, In such devices, it is common to specify the rate or interval ranges that characterize a tachyarrhythmia as opposed to fibrillation. However, some patients may suffer from ventricular tachycardia and ventricular fibrillation that have similar or overlapping rates, making it difficult to distinguish low rate fibrillation from high rate tachycardia. In addition, ventricular fibrillation may display R-R intervals that vary considerably, resulting in intervals that may fall within both the tachycardia and fibrillation rate or interval ranges, or outside both. Similarly, supraventricular arrhythmias may be the cause of high ventricular rates, or may be present during ventricular arrhythmias, further increasing the possibilities of misdiagnosis.

Presently available pacemaker/cardioverter/defibrillator arrhythmia control devices employ programmable fibrillation interval ranges and tachycardia detection interval ranges, along with measurement of suddenness of onset and rate variability. For future generations of devices, numerous detection and classification systems have been proposed. Numerous patents, including U.S. Pat. No. 5,217,021 issued to Steinhaus et al., U.S. Pat. No. 5,086,772 issued to Lanard et al., U.S. Pat. No. 5,058,599 issued to Andersen and U.S. Pat. No. 5,312,441 issued to Mader et al propose waveform morphology analysis systems for determining the type and origin of detected arrhythmias. Other patents, including U.S. Pat. No. 5,205,583 issued to Olson, U.S. Pat. No. 5,913,550 issued to Duffm, U.S. Pat. No. 5,193,535 issued to Bardy et al., U.S. Pat. No. 5,161,527 issued to Nappholz et al., U.S. Pat. No. 5,107,850 issued to Olive and U.S. Pat. No. 5,048,521, issued to Pless et al. propose systems for analysis of order and timing of atrial and ventricular events.

In the Medtronic Model 7219 devices, an arrhythmia detection and classification system generally as disclosed in U.S. Pat. No. 5,342,402, issued to Olson et al., incorporated herein by reference in its entirety, was employed, which uses both strategies together. In currently marketed Medtronic implantable pacemaker/cardioverter/defibrillators, prioritized, rule based arrhythmia classification schemes corresponding generally to those described in U.S. Pat. No. 5,545,186, issued to Olson et al. and U.S. Pat. No. 5,755,736, issued to Gillberg, et al., both incorporated herein by reference in their entireties, are employed.

Classification of detected heart rhythms is also valuable in the context of implantable anti-tachycardia pacemakers which do not include cardioversion or defibrillation capabilities, pacemakers which treat bradycardia, other implantable stimulators, implantable drug dispensers and implantable heart monitors. Examples of arrhythmia classification mechanisms employed in bradycardia pacemakers are disclosed in U.S. Pat. No. 5,282,465, issued to van der Veen, et al., U.S. Pat. No. 5,549,649 issued to Florio, et al., U.S. Pat. No. 5,792,200 issued to Brewer and U.S. Pat. No. 5,144,549, issued to Olson, et al., all incorporated herein by reference in their entireties. In the context of implantable drug dispensers, particularly those in which an anti-arrhythmic drug is delivered, accurate identification of cardiac rhythms is of paramount importance. Such drug dispensers are disclosed in U.S. Pat. No. 4,146,029, issued to Ellinwood and U.S. Pat. No. 5,527,344, issued to Arzbaecher, et al. and U.S. Pat. No. 5,220,917, all incorporated herein by reference in their entireties.

One of the most difficult problems in the design of implantable cardioverter defibrillators (ICDS) and other devices that need to be able to correctly classify cardiac arrhythmias, is the design of mechanisms to discriminate between tachycardias that should be treated and those that should not. For example, sinus tachycardia (ST) should never be treated by an ICD. Particularly in the context of dual chamber bradycardia pacemakers, a determination of whether a detected rapid atrial rhythm is a reentrant tachycardia or a sinus rhythm is valuable in determining whether the pacemaker will deliver ventricular pacing pulses in synchronism with the detected atrial rhythm or switch to a non-synchronized pacing mode. One early original mechanism for discriminating between sinus tachycardia and reentrant atrial or ventricular tachycardia was the onset criterion, as described in the above-cited Olson, et al. '402 patent and in U.S. Pat. No. 4,880,005 issued to Pless, et al. This simple mechanism for discriminating against sinus tachycardia considered only ventricular rate information. As an improvement, the ST Rule as disclosed in the above-cited Olson, et al. '186 patent was created. The ST Rule and the onset criterion as employed in the Olson '186 patent are mutually exclusive in their use of timing information. The ST Rule considered only the timing of P-waves relative to R-waves whereas the onset criterion considered only the timing of R-waves relative to R waves.

SUMMARY OF THE INVENTION

The present invention is directed to a third generation adaptive "New ST rule" that provides a more accurate ST detection mechanism for next generation cardiac pacemakers, ICDS, drug pumps, monitors or other devices. The New ST Rule is a rule which, when met, may control delivery or withholding of therapy. In the particular embodiment disclosed below, the New ST Rule is incorporated into a prioritized, rule-based arrhythmia classification system in an implantable pacemaker/cardioverter/defibrillator. In this particular embodiment, if the New ST Rule is met, antitachyarrhythmia therapy is withheld even if a lower priority rule determines that a treatable tachyarrhythmia is present. In other applications of the New ST rule, it might be employed as part of a mechanism to control delivery of bradycardia pacing. For example, a switch to non-synchronized ventricular pacing might be prevented in the presence of a rapid atrial rate, if the New ST Rule is met. Similarly, the New ST Rule may be employed as an arrhythmia classification mechanism in an implanted drug dispenser, used for example to prevent unneeded increases in anti-tachyarrhythmic drug delivery in response to rapid non-pathological sinus rhythms and may also be used as an arrhythmia classification mechanism in an implanted cardiac monitor.

The New ST Rule comprises an adaptive onset criterion. An "expected range" of RR intervals is calculated based on a trimmed mean and a metric of R-R variability (similar to a standard deviation), derived over a preceding series of R-R intervals. The expected range is updated adaptively after ventricular events. Preferably the expected interval range is not updated during non-1:1 rhythms, as described in more detail below. Thus, during 1:1 rhythms, the expected range of R-R intervals follows the trend of observed R-R intervals as it increases and decreases. Consistent R-R intervals result in a narrow expected range, whereas more variable R-R intervals broaden the expected range. Continued presence of R-R intervals within the expected R-R interval range is inconsistent with the rapid rate change associated with onset of ventricular tachycardia and is considered by the New ST Rule as evidence of sinus rhythm and assists in allowing the New ST rule to ultimately be met. Conversely, downward departures of the R-R intervals from the expected R-R interval range are considered as evidence of the onset of ventricular tachycardia, and correspondingly work to prevent the ST Rule from being met. The ability of the expected interval range to adapt to the underlying degree of variability of the patient's heart rhythm improves the accuracy with which the New ST Rule distinguishes between sinus tachycardia and ventricular tachycardia.

The sensitivity of this adaptive onset criterion provided by the New ST Rule is preferably further augmented by available atrial information. First, consistent non-1:1 rhythms are treated as evidence against the presence of sinus rhythm. Care is exercised to allow for non-sustained ectopy an inappropriate atrial sensing due to the presence of far-field R-waves (FFRW). Second, the New ST Rule monitors for "P-R onset", i.e., a sudden change in the P-R interval, as evidence against the presence of sinus rhythm. An expected range of P-R intervals is established and updated adaptively in a similar manner to the R-R expected range. P-R intervals that fall outside of their expected range are treated as evidence against sinus rhythm. This "P-R onset" feature is beneficial for proper treatment of VT with 1:1 retrograde conduction that does not have a significant ventricular rate onset.

The evidence for sinus rhythm in the embodiment described below is accumulated via beat codes, pattern codes and a continuous recognition machine with exponential decay, similar in general operational aspects to the ST Rule as described in the above-cited Olson et al patent. Pattern codes indicative of gradual rate changes and normal sinus rhythm will adhere to the grammar defined by the continuous recognition machine and will, if they persist, result in the New ST Rule being met. Pattern codes inconsistent with sinus tachycardia, e.g. indicative of non-1:1 rhythms or rapid rate change associated with sudden onset of VT, will not adhere to the associated grammar and will result in the New ST Rule not being met. A more detailed description of a preferred embodiment of the New ST Rule is provided below.

DETAILED DESCRIPTION OF THE PREFERRED EMBODIMENTS

The following description sets forth the incorporation of the New ST Rule into a device generally as described in the above-cited Gillberg, et al. '736 or Olson, et al. '186 patents. It should be understood that New ST Rule and the adaptive onset criterion it provides may also usefully be employed in conjunction with other types of devices and with other types of detection schemes, including those described in the other patents cited above.

In the particular embodiment described herein the New ST Rule is incorporated into an arrhythmia detection and classification system generally as described in the above-cited Olson, et al. '186 or Gillberg, et al. '736 patents, both of which employ a prioritized set of inter-related rules for arrhythmia detection. Each rule contains a set of one or more "clauses" which must be satisfied (criteria which must be met). While all clauses of a rule are satisfied, the rule is indicated to be met. It is possible for multiple rules to be met at the same time, with the highest priority rule taking precedence. Some rules trigger delivery of therapy when met. Other rules inhibit delivery of therapy when met. The highest priority rule met at any specific time controls the behavior of the device. For example, a rule, which triggers therapy, when met, is superseded by higher priority rules preventing delivery of therapy, when met. Rules cease to be met when their clauses cease to be satisfied for a defined number of R-R intervals, whether or not a therapy was triggered by the rule. In such embodiments of the invention, the New ST Rule and the adaptive onset criterion it supplies take the form of one of the prioritized list of rules. In the particular embodiment described, the New ST Rule should be understood as substituted for the ST Rule in a device otherwise as described in the Olson, et al. '186 or Gillberg, et al. '736 patent.

Each rule includes a set of clauses which, when satisfied, indicate the likely occurrence of a specified type of heart rhythm, including various tachyarrhythmias, sinus tachycardia and/or normal sinus rhythm. A specific rhythm or tachyarrhythmia may have more than one associated rule. The rules may be interrelated, such that progress toward meeting the requirements of a clause of one rule may also be the subject matter of a clause of a different rule. In the embodiment of the invention disclosed herein , the New ST Rule should be understood to be a rule that, like the ST rule of the cited prior patents, withholds delivery of therapy if it is the highest priority rule met. Typically, the New ST rule will have higher priority than one or more rules, which, if met, will trigger delivery of anti-tachyarrhythmia therapies. For example, in the specific embodiment disclosed herein, the lower priority rules may include the detection rule set of the Medtronic 7219 defibrillator, as disclosed in the above-cited Olson, et al. '402 patent. A number of evaluation criteria are included within the clauses of various rules.

One methodology, used by the New ST rule and by other rules as described in the above-cited Olson, et al. '186 and Gillberg, et al. '736 patents, is based upon the classification of events associated with sequences of two ventricular depolarizations into a limited number of beat codes, based upon the number and times of occurrences of atrial events between the two most recent ventricular events. For each ventricular event, a beat code is derived based upon the number and timing of atrial events within the R-R interval. Beat codes for the current R-R interval and the previous R-R interval are combined to produce a pattern code. Certain sequences of pattern codes are strongly indicative of specific types of heart rhythms. For heart rhythms of which this is true, a defined set of indicative pattern codes or a "grammar" is defined. Adherence of the heart rhythm to the grammars associated with various heart rhythms is determined by simultaneously operating continuous recognition machines, the outputs of which form the subject matter of one or more clauses, within the hierarchy of rules.

An additional classification criterion employed in conjunction with the New ST Rule comprises a methodology of identifying the likelihood that events sensed in the atrium are in fact far-field R waves, rather than P waves. The occurrence of such identified far-field R waves over a sequence of R-R intervals is employed in conjunction with rules indicative of various types of supra-ventricular tachycardias. The mechanism for identifying Far-field R-waves in context of the New ST Rule is somewhat modified from that described in the Olson, et al. '186 patent, as described below.

The New ST rule is a single clause rule, in which the adaptive onset criteria are employed to define beat codes and pattern codes, which in turn are employed by a continuous recognition machine. When the continuous recognition machine (CRM) of the New ST Rule determines that the defined grammar associated with sinus tachycardia is adhered to, the New ST rule is met. In particular, the CRM is associated with a microprocessor-defined counter, (the ST Evidence Counter) which provides a numerical output indicative of the adherence of the pattern codes to the defined grammar. If the numerical output of the ST Evidence counter meets a defined threshold, the single clause of the New ST rule is satisfied, and the New ST rule is correspondingly met. The New ST rule is a "sticky rule", as defined in the Olson, et al. '186 patent, which when met continues to be met until the single clause of the rule fails to be satisfied for a defined number of R-R intervals, e.g. six.

In this embodiment, while the New ST rule is met, therapies that would otherwise be delivered in response to lower priority rules being met are blocked. Therapies associated with higher priority rules correspondingly take precedence over the New ST Rule. For example, in the context of a device that detects and treats only ventricular tachyarrhythmias, as in the Olson, et al '186 patent, both higher and lower priority rules might trigger therapies for ventricular fibrillation and ventricular tachycardia. In the context of a device as in the Gillberg, et al '736 patent, lower priority rules might trigger therapies for ventricular fibrillation and ventricular tachycardia, while higher priority rules might trigger therapies for supra-ventricular tachycardias, as well as for ventricular fibrillation and ventricular tachycardia. In either case, other rules which block delivery of therapies provided by lower priority rules may also be included.

I. Example of a Device in which the New ST Rule May be Incorporated

Figure 1:
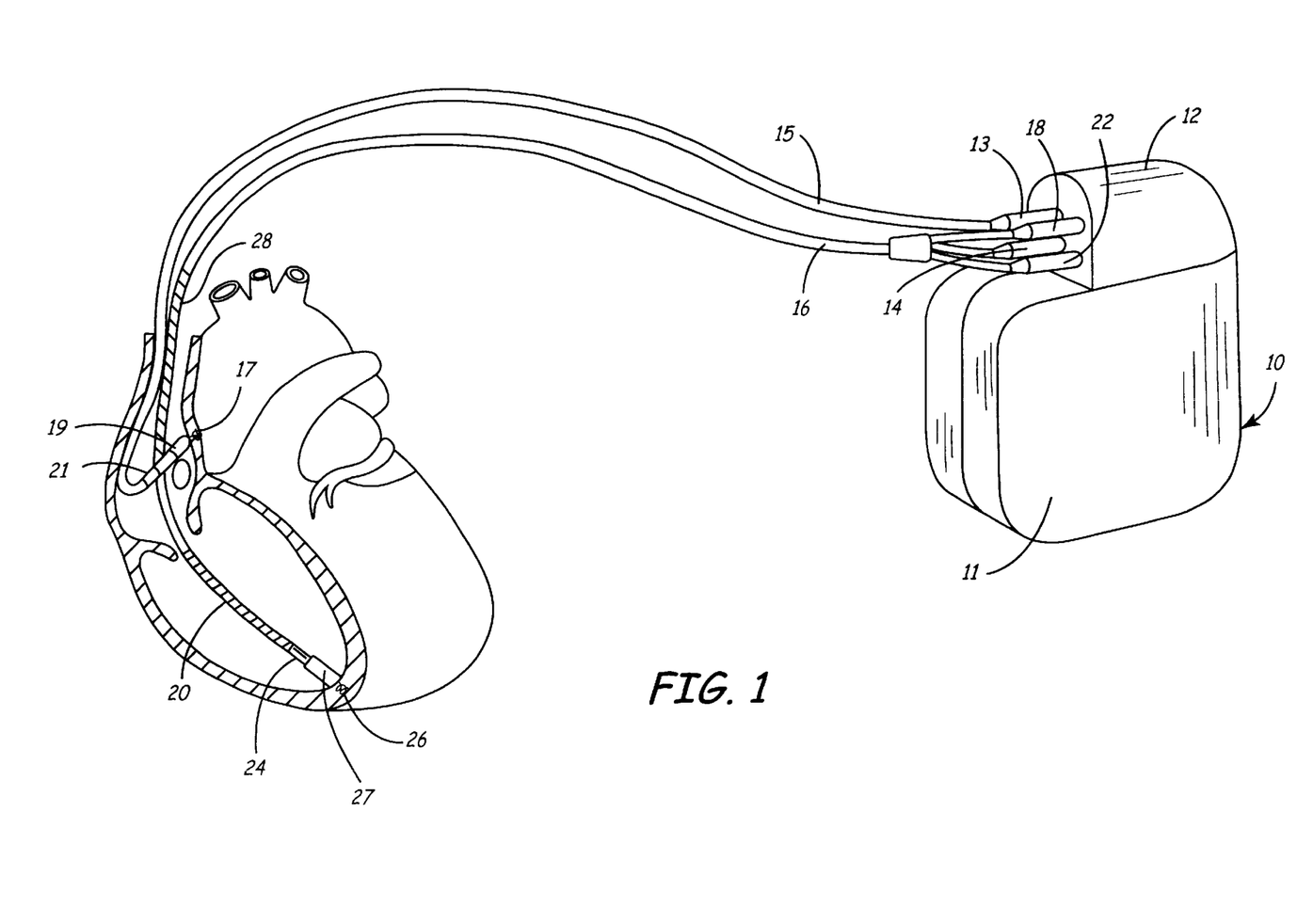
FIG. 1 illustrates a first embodiment of an implantable pacemaker/cardioverter/defibrillator of a type appropriate for use in practicing the present invention, in conjunction with a human heart.

FIG. 1 illustrates an exemplary pacemaker/cardioverter/ defibrillator 10 and lead set in which the present invention may be practiced. The ventricular lead includes an elongated insulative lead body 16, carrying four mutually insulated conductors. Located on the lead body are a ring-electrode 24, an extendable helix electrode 26, mounted retractably within an insulative electrode head 27, and elongated coil electrodes 20 and 28. Each of the electrodes is coupled to one of the conductors within the lead body 16. Electrodes 24 and 26 are employed for cardiac pacing and for sensing ventricular depolarizations. Electrodes 20 and 28 are employed in conjunction with the conductive housing 11 of the pacemaker/cardioverter/ defibrillator 10 for delivery of ventricular cardioversion and defibrillation pulses. At the proximal end of the lead body 16 are two unipolar connectors 18 and 22 which each carry a connector pin coupled to one of the coiled electrodes 20 and 28. Electrical connector 14 is an in-line bipolar connector carrying a connector ring and a connector pin, coupled to electrodes 24 and 26, respectively.

The atrial lead as illustrated is a conventional bipolar atrial pacing lead. The atrial lead includes an elongated insulative lead body 15, carrying two mutually insulated conductors. Located adjacent the J-shaped distal end of the lead are a ring electrode 21 and an extendable helix electrode 17, mounted retractably within an insulative electrode head 19. Each of the electrodes is coupled to one of the coiled conductors within the lead body 15. Electrodes 17 and 21 are employed for atrial pacing and for sensing atrial depolarizations. At the proximal end of the lead is an in-line connector 13, which carries a connector ring, and a connector pin, coupled to electrodes 21 and 17, respectively. In alternative lead systems, a defibrillation electrode, for example corresponding to electrode 28, might instead be mounted to the atrial lead, or might be mounted to a coronary sinus lead, for location in the coronary sinus and great cardiac vein.

An implantable pacemaker/cardioverter/defibrillator 10 is shown in combination with the leads, with the lead connectors 13, 14, 18 and 22 inserted into the connector block 12, which contains corresponding electrical connectors for coupling to the various connector rings and pins. Optionally, insulation of the outward facing portion of the housing 11 of the pacemaker/cardioverter/ defibrillator 10 may be provided in the form of a plastic coating, for example parylene or silicone rubber, as is currently employed in some unipolar cardiac pacemakers. However, the outward facing portion may instead be left uninsulated, or some other division between insulated and uninsulated portions may be employed. The uninsulated portion of the housing 11 serves as a subcutaneous defibrillation electrode, used in conjunction with one or both of electrodes 20 and 28.

Figure 2:
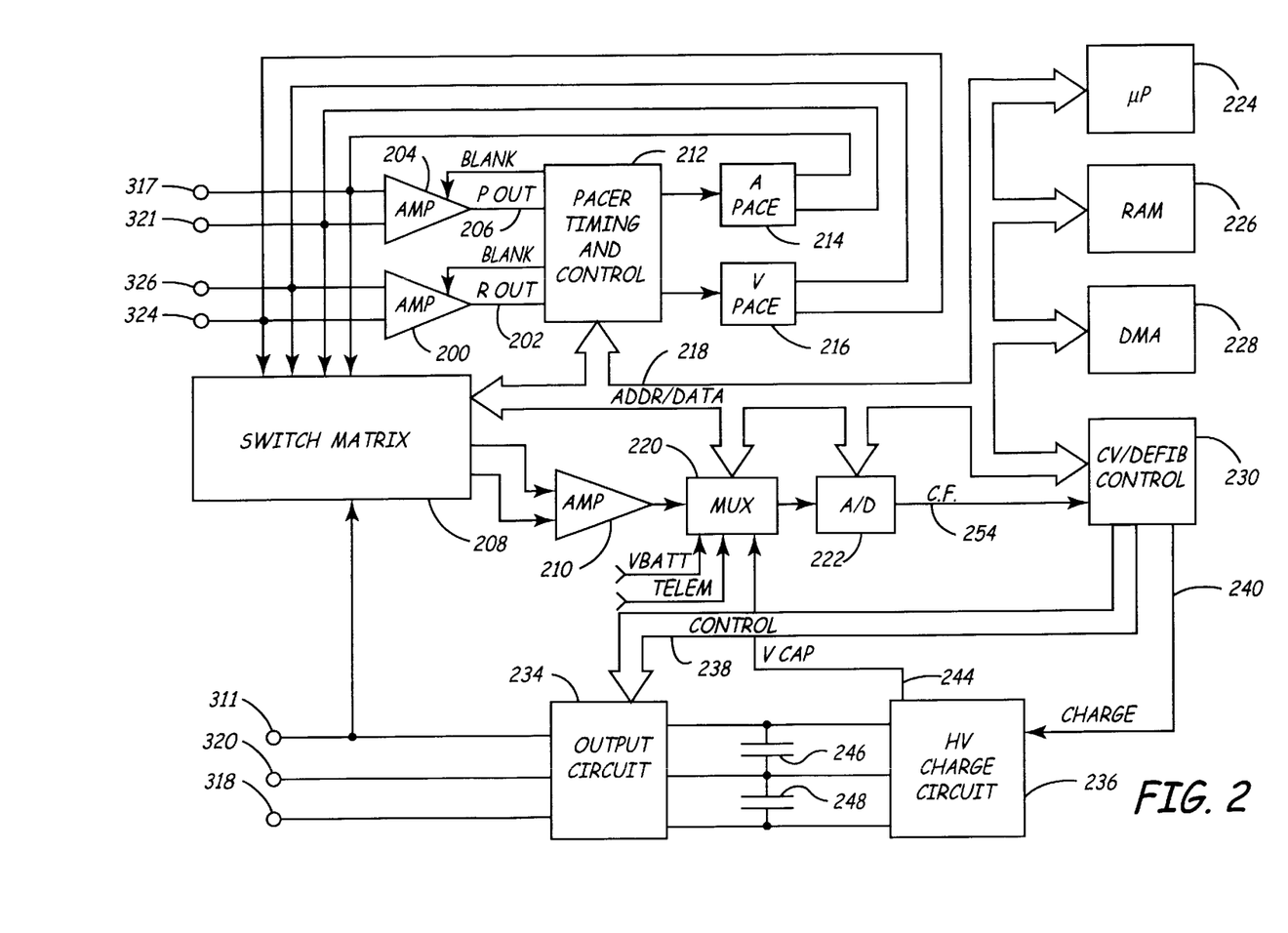
FIG. 2 illustrates a functional schematic diagram of an implantable pacemaker/cardioverter/defibrillator in which the invention may be practiced.

FIG. 2 is a functional schematic diagram of an implantable pacemaker/cardioverter/defibrillator in which the present invention may usefully be practiced. This diagram should be taken as exemplary of one type of device in which the invention may be embodied, and not as limiting, as it is believed that the invention may usefully be practiced in a wide variety of device implementations, including devices providing therapies for treating atrial arrhythmias instead of or in addition to ventricular arrhythmias, cardioverters and defibrillators which do not provide anti-tachycardia pacing therapies, anti-tachycardia pacers which do not provide cardioversion or defibrillation, bradycardia pacemakers, implantable monitors and devices which deliver different forms of anti-arrhythmia therapies such nerve stimulation or drug administration.

The device is provided with a lead system including electrodes, which may be as illustrated in FIG. 1. Alternate lead systems may of course be substituted. If the electrode configuration of FIG. 1 is employed, the correspondence to the illustrated electrodes is as follows. Electrode 311 corresponds to electrode 11, and is the uninsulated portion of the housing of the implantable pacemaker/cardioverter/ defibrillator. Electrode 320 corresponds to electrode 20 and is a defibrillation electrode located in the right ventricle. Electrode 318 corresponds to electrode 28 and is a defibrillation electrode located in the superior vena cava. Electrodes 324 and 326 correspond to electrodes 24 and 26, and are used for sensing and pacing in the ventricle. Electrodes 317 and 321 correspond to electrodes 17 and 21 and are used for pacing and sensing in the atrium.

Electrodes 311, 318 and 320 are coupled to high voltage output circuit 234. Electrodes 324 and 326 are located on or in the ventricle and are coupled to the R-wave amplifier 200, which preferably takes the form of an automatic gain controlled amplifier providing an adjustable sensing threshold as a function of the measured R-wave amplitude. A signal is generated on R-out line 202 whenever the signal sensed between electrodes 324 and 326 exceeds the present sensing threshold.

Electrodes 317 and 321 are located on or in the atrium and are coupled to the P-wave amplifier 204, which preferably also takes the form of an automatic gain controlled amplifier providing an adjustable sensing threshold as a function of the measured R-wave amplitude. A signal is generated on P-out line 206 whenever the signal sensed between electrodes 317 and 321 exceeds the present sensing threshold Switch matrix 208 is used to select which of the available electrodes are coupled to wide band amplifier 210 for use in digital signal analysis. Selection of electrodes is controlled by the microprocessor 224 via data/address bus 218, which selections may be varied as desired. Signals from the electrodes selected for coupling to amplifier 210 are provided to multiplexer 220, and thereafter converted to multi-bit digital signals by A/D converter 222, for storage in random access memory 226 under control of direct memory access circuit 228. Microprocessor 224 may employ digital signal analysis techniques to characterize the digitized signals stored in random access memory 226 to recognize and classify the patient's heart rhythm employing any of the numerous signal-processing methodologies known to the art.

The remainder of the circuitry is dedicated to the provision of cardiac pacing, cardioversion and defibrillation therapies, and, for purposes of the present invention may correspond to circuitry known in the prior art. An exemplary apparatus is disclosed for accomplishing pacing, cardioversion and defibrillation functions as follows. The pacer timing/control circuitry 212 includes programmable digital counters which control the basic time intervals associated with DDD, VVI, DVI, VDD, AAI, DDI and other modes of single and dual chamber pacing well known to the art. Circuitry 212 also controls escape intervals associated with anti-tachyarrhythmia pacing in both the atrium and the ventricle, employing, any anti-tachyarrhythmia pacing therapies known to the art.

Intervals defined by pacing circuitry 212 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 224, in response to stored data in memory 226 and are communicated to the pacing circuitry 212 via address/data bus 218. Pacer circuitry 212 also determines the amplitude of the cardiac pacing pulses under control of microprocessor 224.

During pacing, the escape interval counters within pacer timing/control circuitry 212 are reset upon sensing of R-waves and P-waves as indicated by signals on lines 202 and 206, and in accordance with the selected mode of pacing on time-out trigger generation of pacing pulses by pacer output circuits 214 and 216, which are coupled to electrodes 317, 321, 324 and 326. The escape interval counters are also reset on generation of pacing pulses, and thereby control the basic timing of cardiac pacing functions, including anti-tachyarrhythmia pacing.

The durations of the intervals defined by the escape interval timers are determined by microprocessor 224, via data/address bus 218. The value of the count present in the escape interval counters when reset by sensed R-waves and P-waves may be used to measure the durations of R-R intervals, P-P intervals, PR intervals and R-P intervals, which measurements are stored in memory 226 and used in conjunction with the present invention to diagnose the occurrence of a variety of tachyarrhythmias, as discussed in more detail below.

Microprocessor 224 operates as an interrupt driven device, and is responsive to interrupts from pacer timing/control circuitry 212 corresponding to the occurrences of sensed P-waves and R-waves and corresponding to the generation of cardiac pacing pulses. These interrupts are provided via data/address bus 218. Any necessary mathematical calculations to be performed by microprocessor 224 and any updating of the values or intervals controlled by pacer timing/control circuitry 212 take place following such interrupts. A portion of the memory 226 (FIG. 4) may be configured as a plurality of recirculating buffers, capable of holding series of measured intervals, which may be analyzed in response to the occurrence of a pace or sense interrupt to determine whether the patient's heart is presently exhibiting atrial or ventricular tachyarrhythmia.

The arrhythmia detection method of the present invention may include prior art tachyarrhythmia detection algorithms in addition to or as part of a rule-based detection mechanism as in the present embodiment. For example, as described in the above-cited Olson, et al. '186 and Gillberg, et al. '736 patents, the entire ventricular arrhythmia detection methodology of presently available Medtronic pacemaker/cardioverter/defibrillators may be employed as part of the arrhythmia detection and classification method according to the disclosed preferred embodiment of the invention. However, any of the various arrhythmia detection methodologies known to the art, as discussed in the Background of the Invention section above might also usefully be employed in alternative embodiments of the invention.

In the event that an atrial or ventricular tachyarrhythmia is detected, and an anti-tachyarrhythmia pacing regimen is desired, appropriate timing intervals for controlling generation of anti-tachyarrhythmia pacing therapies are loaded from microprocessor 224 into the pacer timing and control circuitry 212, to control the operation of the escape interval counters therein and to define refractory periods during which detection of R-waves and P-waves is ineffective to restart the escape interval counters. Alternatively, circuitry for controlling the timing and generation of anti-tachycardia pacing pulses as described in U.S. Pat. No. 4,577,633, issued to Berkovits et al on Mar. 25, 1986, U.S. Pat. No. 4,880,005, issued to Pless et al on Nov. 14, 1989, U.S. Pat. No. 7,726,380, issued to Vollmann et al on Feb. 23, 1988 and U.S. Pat. No. 4,587,970, issued to Holley et al on May 13, 1986, all of which are incorporated herein by reference in their entireties may also be used.

In the event that generation of an atrial or ventricular cardioversion or defibrillation pulse is required, microprocessor 224 employs the escape interval counter to control timing of such cardioversion and defibrillation pulses, as well as associated refractory periods. In response to the detection of atrial or ventricular fibrillation or tachyarrhythmia requiring a cardioversion pulse, microprocessor 224 activates cardioversion/defibrillation control circuitry 230, which initiates charging of the high voltage capacitors 246, 248 via charging circuit 236, under control of high voltage charging control line 240. The voltage on the high voltage capacitors is monitored via VCAP line 244, which is passed through multiplexer 220 and in response to reaching a predetermined value set by microprocessor 224, results in generation of a logic signal on Cap Full (CF) line 254, terminating charging. Thereafter, timing of the delivery of the defibrillation or cardioversion pulse is controlled by pacer timing/control circuitry 212. Following delivery of the fibrillation or tachycardia therapy the microprocessor then returns the device to cardiac pacing and awaits the next successive interrupt due to pacing or the occurrence of a sensed atrial or ventricular depolarization.

One embodiment of an appropriate system for delivery and synchronization of ventricular cardioversion and defibrillation pulses and for controlling the timing functions related to them is disclosed in more detail in commonly assigned U.S. Pat. No. 5,188,105 by Keimel, issued Feb. 23, 1993, and incorporated herein by reference in its entirety. If atrial defibrillation capabilities are included in the device, appropriate systems for delivery and synchronization of atrial cardioversion and defibrillation pulses and for controlling the timing functions related to them may be found in PCT Patent Application No. WO92/18198 by Adams et al., published Oct. 29, 1992, and in U.S. Pat. No. 4,316,472 by Mirowski et al., issued Feb. 23, 1982, both incorporated herein by reference in their entireties.

However, any known cardioversion or defibrillation pulse control circuitry is believed usable in conjunction with the present invention. For example, circuitry controlling the timing and generation of cardioversion and defibrillation pulses as disclosed in U.S. Pat. No. 4,384,585, issued to Zipes on May 24, 1983, in U.S. Pat. No. 4,949,719 issued to Pless et al, cited above, and in U.S. Pat. No. 4,375,817, issued to Engle et al, all incorporated herein by reference in their entireties may also be employed, In the illustrated device, delivery of the cardioversion or defibrillation pulses is accomplished by output circuit 234, under control of control circuitry 230 via control bus 238. Output circuit 234 determines whether a monophasic or biphasic pulse is delivered, whether the housing 311 serves as cathode or anode and which electrodes are involved in delivery of the pulse. An example of output circuitry for delivery of biphasic pulse regimens may be found in the above-cited patent issued to Mehra and in U.S. Pat. No. 4,727,877, incorporated by reference in its entirety.

An example of circuitry that may be used to control delivery of monophasic pulses is set forth in commonly assigned U.S. Pat. No. 5,163,427, by Keimel, issued Nov. 17, 1992, also incorporated herein by reference in its entirety. However, output control circuitry as disclosed in U.S. Pat. No. 4,953,551, issued to Mehra et al on Sep. 4, 1990 or U.S. Pat. No. 4,800,883, issued to Winstrom on Jan. 31, 1989 both incorporated herein by reference in their entireties, may also be used in conjunction with a device embodying the present invention for delivery of biphasic pulses.

In the event that fibrillation is identified, the typical therapy will be delivery of a high amplitude defibrillation pulse, typically in excess of 5 joules. Lower energy levels may be employed for cardioversion. As in the case of currently available implantable pacemakers/cardioverter/defibrillators, and as discussed in the above-cited references, it is envisioned that the amplitude of the defibrillation pulse may be incremented in response to failure of an initial pulse or pulses to terminate fibrillation. Prior art patents illustrating such pre-set therapy menus of anti-tachyarrhythmia therapies include the above-cited U.S. Pat. No. 4,830,006, issued to Haluska, et al., U.S. Pat. No. 4,727,380, issued to Vollmann et al. and U.S. Pat. No. 4,587,970, issued to Holley et al.

Alternative embodiments of devices which may employ the new ST Rule may include, as discussed above, bradycardia pacemakers and implantable heart monitors. In such embodiments, the devices employing the New ST Rule may generally include a subset of the elements of the apparatus illustrated in FIGS. 1 and 2. However, it should be kept in mind that pacemaker/cardioverter/defibrillators as generally disclosed above also function as implantable bradycardia pacemakers and an implantable heart monitors.

For example, in the case of a dual chamber cardiac pacemaker incorporating the New ST Rule, the device might only include those elements illustrated in FIG. 2 which are related to cardiac sensing, pacing and arrhythmia analysis and may omit those elements associated with delivery of cardioversion and defibrillation pulses. In such case, all or part of the arrhythmia classification scheme described above may be retained for diagnostic purposes. The New ST rule in such embodiments, or in ICD embodiments as described above, may also be employed as part of a mode-switching mechanism, in which, for example, switching to non-synchronized ventricular pacing in the presence of a rapid atrial rate might be prevented in response to the New ST Rule being met. Alternatively, if the ST Rule is met, a higher atrial rate might be required as a prerequisite to mode switching and/or other additional criteria might have to be met as a prerequisite to mode switching.

In the case of an implantable heart monitor incorporating the New ST Rule, the device might only include those elements illustrated in FIG. 2 related to cardiac sensing and arrhythmia analysis and may omit those elements associated with delivery of cardioversion, defibrillation and pacing pulses. In such case, all or part of the arrhythmia classification scheme described above may be retained for diagnostic purposes.

In the context of an implantable drug dispenser, nerve stimulator or other implantable device, those elements of FIG. 2 related to cardiac sensing and arrhythmia analysis may be retained a drug pump and reservoir or a nerve stimulator and associated control logic may be substituted for the elements of FIG. 2 related to cardiac pacing, cardioversion and defibrillation.

Figure 3:
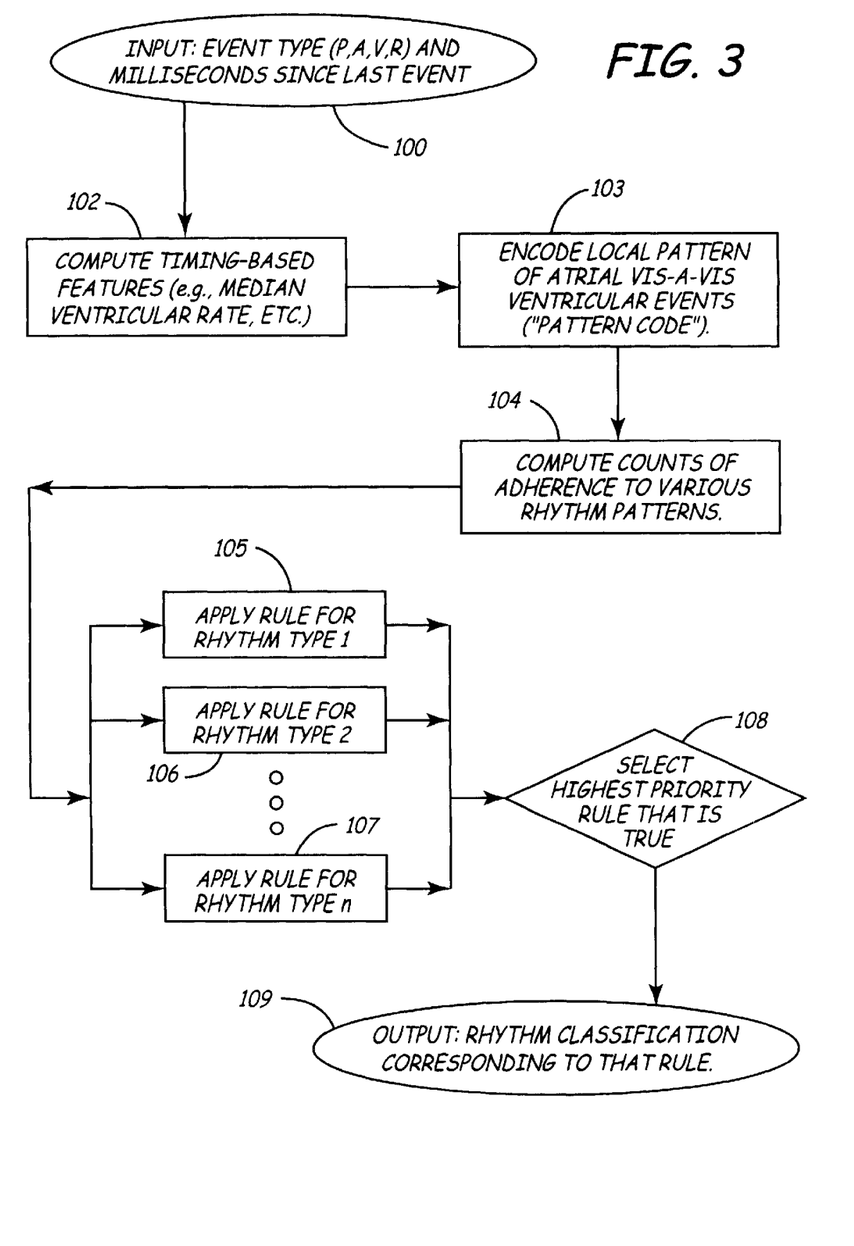
FIG. 3 illustrates the over-all operation of a device in which the invention may be practiced.

FIG. 3 illustrates the basic operation of a device as generally described in the above-cited Olson, et al. '186 and Gillberg, et al. '736 patents as discussed above. The disclosed embodiment of the present invention, having a general operating scheme taken from the devices disclosed in these two patents, operates in the same fashion. In response to an atrial or ventricular event at 100, the type of event is stored, and also a number of counts and values referred to above are updated. In particular, in response to an atrial or ventricular event, the processor stores information as to the number of atrial events received since the last ventricular event, the count of the number of ventricular events received since the last atrial event, and R-R, R-P, P-P and P-R intervals, as appropriate. The processor maintains buffers in the RAM, in which the following information is stored: recent P-P intervals, R-R intervals, R-P intervals P-R intervals and the times of occurrence of atrial and ventricular events over the preceding R-R intervals, employed in conjunction with the detection of tachyarrhythmias as discussed below.

At 102, the processor updates all timing based features associated with the occurrences of atrial and ventricular events, including all computations necessary to update the buffers described above. In addition to these functions, in response to the occurrence of a ventricular event, as part of the processor at 103 computes beat codes and corresponding pattern codes associated with the R-R interval ending with the ventricular event and at 104 updates the continuous recognition machines, as described above and computes all timing based values associated with the Model 7219 detection criteria described below, including updating of the value of VTEC, VFEC, the onset and stability counters. The processor now has stored in RAM all information necessary to apply the hierarchical set of rules used to identify the particular type of rhythm under way.

At 105, 106, 107, the processor determines which of the various available rules have all of their respective clauses satisfied. As discussed above, one, more than one, or no rules may have their causes all satisfied. If more than one rule is met, the rule of highest priority is selected at 108, leading to a rhythm classification corresponding to that rule at 109. If anti-arrhythmia therapies are enabled, in response to the classification of the rhythm, the device delivers therapy or prevents delivery of therapy, depending upon the rhythm identified. In any case, the device stores information with respect to the fact that the rule was met for later telemetry to an external device, to be used by the physician for diagnostic purposes. In the absence of any rules being identified, the device withholds anti-tachyarrhythmia therapy. If the device is programmed to provide bradycardia backup pacing, it continues to do so. If not, the device simply continues to monitor the rhythm of the heart, until one or more rules is met.

In the context of devices operating in this manner, many possible rhythm classifications may be provided by the rule set. These include ventricular fibrillation, fast ventricular tachycardia, ventricular tachycardia, A-V nodal tachycardia, sinus tachycardia, atrial fibrillation, atrial flutter, atrial tachycardia, non-specific supra-ventricular tachycardias and the like, as described in the Olson, et al '186 and Gillberg, et al. '736 patents.

II. New ST Rule—Underlying Parameters
A. 7219 Detection Rules

In the embodiment disclosed herein, input to the New ST Rule includes criteria based upon underlying rate-based parameters. In the specific embodiment disclosed, it should be understood that, as in the above-cited Olson, et al. '186 and Gillberg, et al '736 patents, rules with lower priority than the New ST Rule include the detection rules for the Medtronic Model 7219 ICD. The criteria for detection of ventricular fibrillation, fast ventricular tachycardia and ventricular tachycardia according to this methodology comprise the three lowest priority rules employed for arrhythmia detection and classification. If any of these rules is the highest priority rule met delivery of ventricular anti-tachyarrhythmia therapies as programmed occurs, including anti-tachycardia pacing, cardioversion and defibrillation These rules operate as follows and also provide input to the New ST Rule, as discussed below.

In the present embodiment, the R-R interval range designated as indicative of fibrillation consists of R-R intervals less than a programmable interval (FDI) and the interval range designated as indicative of ventricular tachycardia consists of R-R intervals less than a programmable interval (TDI) and greater than or equal to FDI. R-R intervals falling within these ranges are measured and counted to provide a count (VTEC) of R-R intervals falling within the ventricular tachycardia interval range and a count (VFEC) of the number intervals, out of a preceding series of a predetermined number (FEB),of intervals, which fall within the ventricular fibrillation interval range. VTEC is incremented in response to R-R intervals that are greater than or equal to FDI but shorter than TDI, is reset to zero in response to intervals greater than or equal to TDI and is insensitive to intervals less than FDI. VTEC is compared to a programmed value (VTNID) and VFEC is compared to a corresponding programmable value (VFNID). When one of the counts equals its corresponding programmable value, the device diagnoses the presence of the corresponding arrhythmia, i.e. tachycardia or fibrillation and delivers an appropriate therapy, e.g. anti-tachycardia pacing, a cardioversion pulse or a defibrillation pulse. In addition, the physician may optionally require that the measured R-R intervals meet a rapid onset criterion before VTEC can be incremented and can also optionally require that should a rate stability criterion fail to be met, VTEC will be reset to zero. If the device is further programmed to identify the occurrence of a fast ventricular tachycardia, detection of ventricular fibrillation or tachycardia according to the above method serves as a provisional detection, which may be modified, as discussed below.

In addition to the tachycardia and fibrillation detection criteria (VTEC>=VTNID, VFEC>=VFNID) discussed above, detection of tachycardia or fibrillation detection may also be accomplished using a combined count of all intervals indicative of tachycardia or fibrillation. This combined count (VFEC+VTEC) is compared to a combined count threshold (CNID). If VTEC+VFEC is equal or-greater than CNID, the device checks to see whether VFEC is at least a predetermined number (e.g. 6). If so, the device checks to determine how many of a number (e.g. 8) of the immediately preceding intervals are greater or equal to FDI. If a predetermined number (e.g. 8) are greater than or equal to FDI, tachycardia is detected, otherwise ventricular fibrillation is detected. If the device is further programmed to identify the occurrence of a fast ventricular tachycardia, detection of ventricular fibrillation or tachycardia according to the above method serves as a provisional detection, which may be modified, as discussed below.

In addition, the device is provided with a method of distinguishing a fast ventricular tachycardia from either ventricular fibrillation or slow ventricular tachycardia. In conjunction with fast ventricular tachycardia detection, the physician determines whether detection of a fast ventricular tachycardia is to be accomplished following a provisional diagnosis of ventricular tachycardia, following a provisional diagnosis of ventricular fibrillation, or following either. If detection of fast ventricular tachycardia is enabled, then following provisional detection of ventricular tachycardia or fibrillation, as discussed above, the immediately preceding measured intervals are examined to determine whether the provisional detection of fibrillation or tachycardia should be confirmed or amended to indicate detection of fast ventricular tachycardia.

If fast ventricular tachycardia detection following a provisional detection of ventricular tachycardia is enabled, a value FTDImax is defined, which is greater than or equal to FDI. If fast ventricular tachycardia detection following a provisional detection of ventricular fibrillation is enabled, a value FTDImin, is defined, which is less than or equal to FDI. If ventricular tachycardia is provisionally detected, intervals less than FTDImax are taken as indicative of fast ventricular tachycardia. If ventricular fibrillation is provisionally detected, intervals greater than or equal to FTDImin are taken as indicative of fast ventricular tachycardia.

If fibrillation was provisionally detected, the device may require that at least 7 or all 8 of the preceding 8 intervals fall within the fast ventricular tachycardia interval range (greater than or equal to FTDImin) to detect fast ventricular tachycardia. Otherwise, the provisional detection of ventricular fibrillation is confirmed. If ventricular tachycardia is provisionally detected, the device may only require that at least 1 or 2 of the preceding 8 intervals fall within the fast ventricular tachycardia interval range (less than FTDImax in order to detect fast ventricular tachycardia. Otherwise, the provisional detection of (slow) ventricular tachycardia is confirmed.

If ventricular fibrillation is detected according to the above scheme, the "VF Rule" is considered to be met. Unless prevented by the New ST Rule or other higher priority rule intended to prevent treatment being met, the device will in response trigger delivery of a defibrillation pulse. If fast ventricular tachycardia is detected according to the above scheme, the "FVT Rule" is considered to be met. Unless prevented by the New ST Rule or other higher priority rule intended to prevent treatment being met, the device will in response trigger delivery of a cardioversion pulse or an anti-tachycardia pacing therapy. If ventricular tachycardia is detected according to the above scheme, the "VT Rule" is considered to be met. Unless prevented by the New ST Rule or other higher priority rule intended to prevent treatment being met, the device will similarly trigger delivery of a cardioversion pulse or an anti-tachycardia pacing therapy.

B. Far-field R-waves

In conjunction with the operation of the New ST Rule in the present embodiment, the microprocessor also keeps track of the number of R-R intervals that likely contain sensed atrial events caused by far-field R-waves (FFRW), out of a preceding series of R-R intervals. The microprocessor determines that an event sensed in the atrium is likely a far-field R-wave according to the following methodology.

In response to the occurrence of an R-R interval having exactly two P-waves, the microprocessor compares the associated stored values of the R-P and P-R intervals within the R-R interval to fixed thresholds. For example, the processor may check to determine whether the P-R interval is less than or equal to a preset duration, e.g. 60 milliseconds or whether the R-P interval is less than or equal to a preset duration, e.g. 160 milliseconds. It should be kept in mind that in conjunction with an R-R interval having two P-waves, the R-P interval is measured between the ventricular event initiating the R-R interval and the first occurring atrial event and the P-R interval is measured between the second to occur atrial event and the ventricular event ending the R-R interval.

If the P-R interval is less than or equal to 60 milliseconds, the processor compares the P-R interval to the average duration (PRave) of the eight most recent P-R intervals which are also less than 60 milliseconds. If the absolute value of the difference between the P-R interval and this PRave is less than or equal to 20 milliseconds, the processor then subtracts the shortest PR interval (PRmin) out of the preceding eight PR intervals less than 60 milliseconds from the PR interval having the greatest duration (PRmax.) out of the eight most recent intervals less than 60 milliseconds. If the difference between PRmax and PRmin is less than or equal to a preset duration, e.g. 50 milliseconds, the processor compares the P-P interval (PP2) between the two atrial events during the R-R interval under consideration with the P-P interval (PP1) separating the first atrial event in the R-R interval in consideration from the last atrial event in the proceeding R-R interval. If the absolute difference between these two values is greater than or equal to a preset duration, e.g. 30 milliseconds, the processor determines that the R-R interval under consideration likely includes a far-field R-wave.

Similarly, if the measured R-P interval in the R-R interval under question is less than or equal to 160 milliseconds, the processor subtracts the average (RPave) of the eight most recent R-P intervals less than 160 milliseconds from the R-P interval in the RR interval under consideration. If the absolute value between the R-P interval and RPave is less or equal to a preset duration, e.g. 20 milliseconds, the processor checks to determine whether the maximum R-P interval (RPmax) of the eight most recent RP intervals less than 160 milliseconds exceeds the minimum RP interval (RPmin) of the eight most recent RP intervals less than 160 milliseconds by a preset duration, e.g. 50 milliseconds or less. If so, the processor compares the P-P interval (PP2) in the R-R interval under question with the P-P interval (PP1) separating the final atrial event of the preceding R-R interval to the first atrial event of the R-R interval under question. If, as discussed above, the absolute difference between PP1 and PP2 is greater than or equal to 30 milliseconds, the R-R interval under question is determined to likely contain a far-field R wave.

The processor keeps track of the number of R-R intervals out of a preceding series of intervals (e.g., 12 intervals) that likely contain a far-field R wave. As part of the New ST Rule, this number (Far-field R-wave Counter) is compared to a threshold value (Far R Threshold, e.g., 3) to determine whether it is likely that a heart rhythm which appears to have a high atrial rate is in fact the result of far-field R wave sensing.

III. New ST Rule—Operation of Rule

Following each ventricular event, paced or sensed, the microprocessor employs the stored information relating to timing and occurrences of atrial and ventricular events to determine which of the various defined rules associated with heart rhythm classification are met. Evaluation of the patient's cardiac rhythm to determine whether the New ST Rule is met comprises several steps. The first step comprises determining whether the patient's rhythm is 1:1 and whether the Current R-R Interval is within its expected range. The expected R-R interval range is also updated as a part of this step. The second step comprises determining whether the Current P-R interval is within its expected range. The expected P-R interval range is also updated as a part of this step. The third step is to determine a beat code for the Current R-R Interval, using the information derived in steps 1 and 2. The fourth step is to determine a pattern code using the information derived in step 3. The fifth step comprises updating the state of the continuous recognition machine for the New ST Rule, based upon the information derived in the fourth step. This step includes comparing the numerical value of the ST Evidence Counter to a defined threshold to determine whether the single clause of the rule is satisfied and whether the New ST Rule is met.

Step 1 Determine Whether the Rhythm is 1:1 and the Current R-R Interval is as Expected Two conditions must be met for the current R-R interval to be classified as 1:1, in conjunction with this aspect of the New ST Rule. Condition 1 is that the R-R interval ending in the current ventricular event (Current R-R Interval) must have either 1 P-wave or 2 P-waves therein. R-R intervals containing 2 P-waves are allowed as evidence of sinus tachycardia to allow for the case of far-field R-wave sensing by the atrial sense amplifier. Condition 2 is that the recent history must be consistent with 1:1 rhythm (or 2:1 in the presence of far-field R-wave sensing). This condition is met when the RR121 Counter, described below, is greater than 10. If the two conditions are not both met, the Current R-R Interval is classified as shorter than the expected R-R interval range or "short", as discussed below, and the remainder of Step 1, including any updating of the expected R-R interval range, is skipped.

The RR121 Counter is defined by the microprocessor and accumulates evidence that the current rhythm is 1:1. The RR121 Counter is initialized with a value of 10. For each current ventricular event ending an R-R interval that either contains 1 P-wave or 2 P-waves when the Far-field R-wave Counter described above is greater than 3/12, the RR121 Counter is incremented. The RR121 Counter is decremented for each ventricular event ending an R-R interval that does not meet these conditions. If the current value of the RR121 Counter is less than 8 and the R-R interval ending with current event meets the conditions for incrementing the RR121 Counter, the RR121 Counter is given the value of 8. The maximum value of the RR121 Counter is 20 and the minimum value is –20. If the RR121 Counter hits –20 at any time, the R-R interval expected range is placed in reset mode as described below. This signifies that a sustained non-1:1 rhythm is present and any expected R-R interval range defined as a function of a prior 1:1 rhythm will not be valid when and if a 1:1 rhythm is eventually re-established. As noted above, the expected R-R interval range does not adapt when the rhythm is not 1:1.

Each Current R-R Interval that meets the above conditions and is classified as indicative of a 1:1 rhythm is compared by the microprocessor to the expected R-R interval range. The expected R-R interval range is comprised of two parameters, a running trimmed mean R-R interval duration (RRmean) and a running mean absolute difference (RRmad), which is the running mean of the absolute difference between the duration of the Current R-R Interval and RRmean. The expected R-R interval range is the RRmean+/– 2*RRmad. The Current R-R Interval duration is compared to the expected RR interval range before the expected R-R interval range is updated. The Current R-R Interval is classified as +1 ("long"), 0 ("expected"), or –1 ("short"), based upon whether the Current R-R interval is above, within or below the expected R-R interval range. If the Current R-R Interval duration is not within twice the expected range (i.e., RRmean +/–4* RRmad), it is not employed to calculate an updated value of RRmean or to update the expected R-R interval range. This is a way of making the RRmean function as a "trimmed mean".

If the Current R-R Interval duration is within twice the expected R-R interval range, the current value of RRmean and the current value of RRmad are then updated by the microprocessor using the following first order lowpass filter equation:

$$AD=|RR[t]-RRmean[t-1]|$$

$$RRmean[t]=X*RRmean[t-1]+(1-X)*RR[t]$$

$$RRmad[t]=Y*RRmad[t-1]+(1-Y)*(AD+1/32*RRmean[t-1])$$

where t is the current time and X and Y are coefficients that control the rate of adaptation. The nominal values for X and Y are 3/4 and 15/16, respectively. These values may temporarily change when the expected range is reset, as described below. Finally, the range of the RRmad is constrained so that the width of the expected range (i.e., 4 times RRmad) is between 1/8 and 1/4 of the current value of RRmean. Constraining he width of the expected range to be 1/8 to 1/4 of the current value of RRmean is analogous to constraining the effective onset threshold to lie between 87.5% and 75%. This is because a sudden decrease in R-R interval that falls outside of twice the expected RR interval range (RRmean –4*RRmad) will halt the adaptive process and present evidence against sinus rhythm.

Sinus rhythms that are highly variable will have an effective onset threshold near 75%, whereas sinus rhythms that are substantially constant will have an effective onset threshold near 87.5%. The design of this adaptive effective onset threshold is consistent with the relevant underlying physiology of the heart. A high level of parasympathetic tone results in greater heart rate variability and faster available rates of sinus rhythm acceleration. Therefore, patients that can rapidly accelerate their sinus rate will have a lower effective onset threshold (toward 75%). In contrast, low levels of parasympathetic tone imply lower heart rate variability and decreased ability to accelerate sinus rate. This condition will result in a higher effective onset threshold (toward 87.5%).

Because a Current R-R Interval duration must fall within twice the expected RR interval range in order to participate in the adaptation process, it is possible that the expected RR interval range may become "lost" after a step change in R-R interval. To avoid this situation, an RRlost Counter is maintained by the microprocessor. The RRlost Counter is a running sum of the preceding R-R interval classifications (+1 for long, 0 for expected, and –1 for short). A long R-R interval increases the RRlost Counter, a short R-R interval that is longer than TDI (or, FDI if VT detection is off) decreases the RRlost Counter, a short R-R interval that is shorter than TDI (or FDI if VT detection is off) has no effect on the RRlost Counter, and an expected R-R interval moves the RRlost Counter toward zero. The maximum absolute value of the RRlost Counter is 3 times the VTNID (or 3 times the VFNID if VT detection is off). If the RRlost Counter reaches a positive value that is 1/2 of the VTNID (or 1/2 of the VFNID if VT detection is off), the expected range is considered lost in the presence of shorter R-R intervals than the current rhythm. In this situation, RRmean is instantly increased by 2 times the RRmad, thus moving the expected RR interval range to include slower heart rates. If the RRlost counter reaches a negative value that is 3 times the VTNID (or 3 times the VFNID if VT detection is off), the expected R-R interval range is considered to be lost in the presence of R-R intervals longer than the current rhythm, and RRmean is instantly decreased by 2 times the RRmad, thus moving the expected range to include faster heart rates. It should be noted that increasing the expected R-R interval range requires much less evidence than decreasing the expected R-R interval range. This is to ensure that dangerous fast rhythms are not found to be acceptable by the algorithm. The expected R-R interval range will never move into the tachy zone as a result of being "lost," because events in the tachy zone do not affect the RRlost counter.

The process of adaptation of the expected R-R interval range will temporarily enter "reset" mode when the detection algorithm is first turned on, after termination of a tachyarrhythmia episode, or when the RR121 Counter hits –20. When the adaptation process is switched to reset mode, RRmad is set at 150 ms, and an RRreset timer is set to 5. For each R-R interval submitted to the adaptation process, if the RRreset timer is greater than zero and the R-R interval is longer than TDI (or FDI if VT detection is off), the coefficients that control the rate of adaptation (X and Y, mentioned above) take on the values of 0.5, the constraints on the size of the RRmad are removed, and the RRreset timer is decremented. Thus, entry into the reset mode instantly expands the allowed R-R interval range and increases the adaptation rate for 5 ventricular events. If an R-R interval is shorter than TDI (or FDI if VT detection is off) during the reset process, that interval is not included in the adaptation process and is classified as a short interval. Therefore, if detection is initiated after induction of a ventricular arrhythmia that is in the tachycardia detection zone, adaptation will not occur and the ST Rule will not withhold therapy.

As an example of the use of the Reset feature, consider a patient that converts from sinus rhythm to atrial fibrillation (AF). While in AF, the expected R-R interval range will cease to adapt because the AF rhythm will not meet the conditions for inclusion in the adaptation process, described above. If the RR121 Counter is +20 when AF begins, at least 41 ventricular events during AF will be required to decrement the RR121 Counter to −20, which triggers entry into the reset mode. Thus, if less than 41 ventricular events during atrial fibrillation occur before the rhythm converts back to a sinus rhythm, the prior expected R-R interval range will apply to events after sinus rhythm resumes. If more than 40 ventricular events during atrial fibrillation occur before the rhythm converts back to sinus rhythm, the R-R interval expected range will be reset and rapidly reach a new state once sinus rhythm is resumed.

Figure 4:
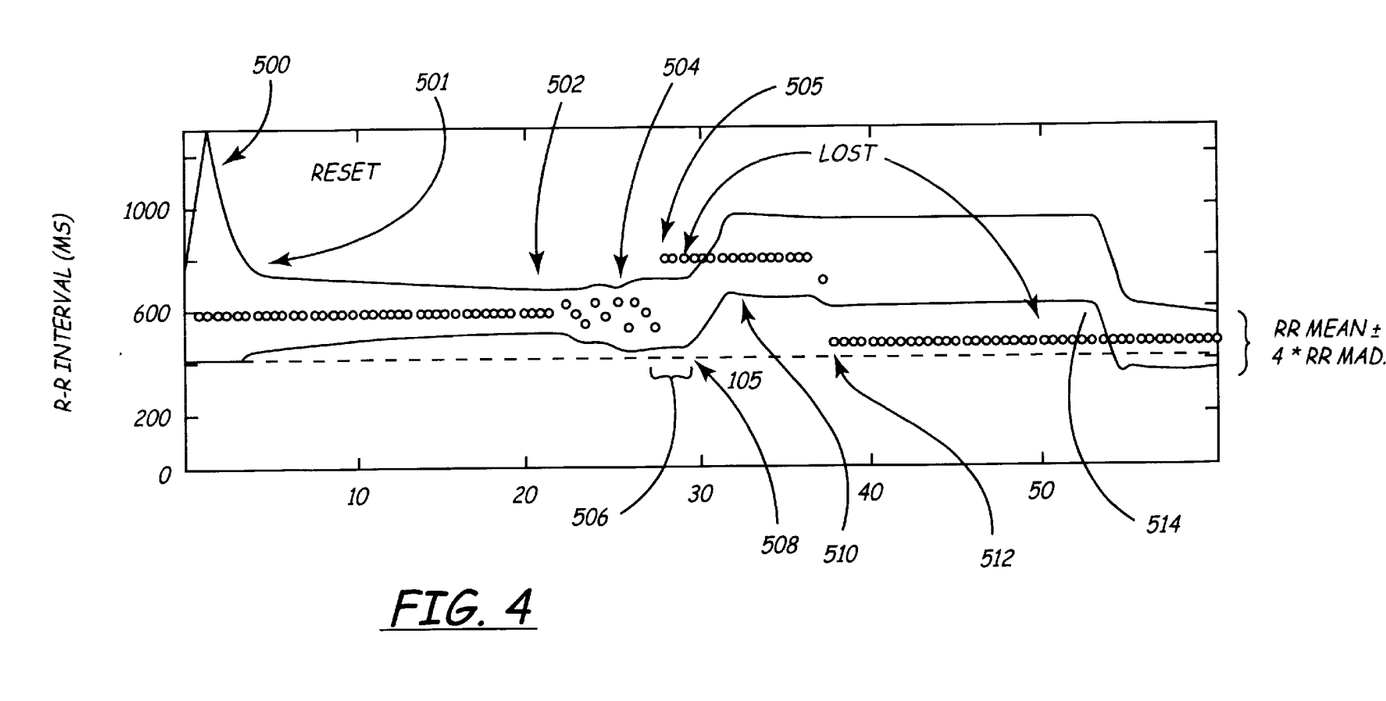
FIG. 4 is a graph illustrating the operation of the New ST Rule in defining an adaptive onset threshold.

FIG. 4 illustrates the operation of the expected R-R interval range and the mechanism by which it is adapted. The dots indicate individual R-R intervals and the boundaries defined by RRmean±4*RRmad are illustrated. As discussed above, R-R intervals falling outside these boundaries are not employed to update the expected R-R interval range. The expected R-R interval range (RRmean±2*RRmad) varies corresponding to but within the illustrated boundaries.

The detection mechanism begins in the Reset state at 500, where the expected R-R interval range is wide and adaption to an initial state at 501 is rapid. Because the R-R intervals are quite consistent, the expected R-R interval range and the boundaries constrict until 4*RRmad equals RRmean/8 at 502. At 504, the R-R intervals become more variable and the expected R-R interval range and the boundaries expand accordingly, with the result that a larger decrease in R-R interval is required to result in a detection of onset of a ventricular tachycardia. At 505, the R-R intervals abruptly increase to a duration outside the boundaries (RRmean±4*RRmad) and the expected R-R interval range remains unchanged during time period 506 until the expected R-R interval range is declared to be "lost" at 508. The expected R-R interval range is then rapidly increased at 510 to include the detected R-R intervals, as discussed above. The sequence is repeated in response to an abrupt decrease in R-R interval at 512, with the expected R-R interval remaining unchanged until declared "lost" at 514.

Step 2 Determine if the Current P-R Interval Is as Expected

A VT with 1:1 VA conduction or nearly 1:1 rhythm and the absence of a R-R interval onset will not be detected by the algorithm as described thus far. The detection sensitivity of the algorithm is therefore augmented by searching for sudden changes in the P-R interval.

If there are no P-waves or more than two P-waves in the current R-R interval, P-R intervals are not considered. If there is a single P-wave in the current R-R interval, that P-wave is selected for comparison with the expected P-R interval. If there are 2 P-waves in the current R-R interval, the P-wave that is closest to the current PRmean (the current running mean of P-R intervals) is selected. However, if one of the two P-waves is located in the far-field R-wave range (i.e., less than 60 ms before or less than 160 ms after the R-wave), the other P-wave is always selected.

Two conditions are required for comparison of the current P-R interval to the expected P-R interval and for inclusion in the adaptation process. Any beat that does not meet these conditions is classified as having its P-R interval within the expected P-R interval range. This is because the P-R interval is used only to augment the sensitivity of the algorithm. If the P-R interval information is unusable, it should not be counted as evidence against the presence of sinus rhythm.

The first condition is that the current R-R interval cannot contain any pacing intervention (including atrial or ventricular pacing but excluding safety pacing), and must contain either 1 P-wave or 2 P-waves when the Far-field R-wave Counter is at least 4/12. The second condition is that recent history must be consistent with a non-paced 1:1 rhythm (or 2:1 in the presence of far-field R-waves). This condition is met when the PR121 Counter is greater than 10. The PR121 Counter is a microprocessor-defined counter that accumulates evidence that the current rhythm is 1:1 and contains no pacing intervention. The PR 121 Counter is initialized with a value of 10. For each R-R interval that contains no pacing but contains either 1 P-wave or 2 P-waves when the Far-field R-wave Counter is greater than 3/12, the PR121 Counter is incremented. The PR121 Counter is decremented for each R-R interval that does not meet these conditions. If the current value of the PR121 Counter is less than 8 and the current R-R interval meets the conditions for incrementing the PR121 Counter, the PR121 Counter is given the value of 8. The maximum value of the PR121 Counter is 20 and the minimum value is −20. If the PR 121 Counter hits −20 at any time, the expected P-R interval range is reset as described below. For example, if intrinsic sinus rhythm becomes predominantly paced, the PR121 Counter will decrease and the two conditions for adaptation of the expected P-R interval range will not be met. During pacing, therefore, P-R interval information will no longer contribute to the New ST Rule. If pacing is prolonged so that the PR 121 Counter hits −20, a new expected P-R interval range will be established by reset mode when intrinsic rhythm is reestablished.

A P-R interval selected as described above and which passed the inclusion criteria described above is then compared to the expected P-R interval range. The expected P-R interval range is comprised of two parameters, PRmean and PRmad (the current running mean absolute difference of P-R intervals). The expected P-R interval range is set equal to PRmean+/−2*PRmad. The current P-R interval is compared to the expected P-R interval range before the expected P-R interval range is updated. The current P-R interval is classified as 0 ("expected"), if within the expected range or 1 ("unexpected") if outside the range. If the current P-R interval is not within twice the expected P-R interval range (i.e., PRmean+/−4*PRmad), it is excluded from the adaptation process (this is to obtain a "trimmed mean", as described above). PRmean and PRmad are then updated by the following first order lowpass filter equation:

$AD=|PR[t]-PRmean[t-1]|$, $PRmean[t]=X*PRmean[t-1]+(1-X)*PR[t]$, $PRmad[t]=Y*PRmad[t-1]+(1-Y)*(AD)$.

When the device is programmed to operate with "high P-R onset sensitivity," the nominal values for X and Y are 15/16. These values temporarily change when the expected range is "reset". PRmad is constrained to be at least 10 ms but no more than 30 ms, except during the "reset" state. The upper limit on PRmad serves to exclude idioventricular rhythms that are 1:1 or nearly 1:1 from being classified as sinus rhythm. When the device is programmed to operate with "low P-R onset sensitivity," the nominal values for X and Y are 7/8, and PRmad is constrained to be at least 20 ms but no more than 30 ms, except during the "reset" state.

Because each P-R interval must fall within twice the expected P-R interval range in order to participate in the adaptation process, it is possible that the expected P-R interval range could become "lost" after a step change in measured P-R interval. To avoid this situation, a PRlost counter is maintained. The PRlost counter is incremented for each R-R interval in which the P-R interval is outside of the expected P-R interval range. The PRlost counter is decremented (until it is zero) for each R-R interval in which the P-R interval is inside the expected P-R interval range. If the PRlost counter reaches three times the VTNID (or three times the VFINID If VT detection is off), the P-R interval expected range is "reset", as discussed below.

When the detection algorithm is first turned on, when an episode is terminated, when the PR121 Counter hits −20 , or when the PRlost counter hits 3 times the VTNID (or 3 times the VFNID if VT detection is off), the expected P-R interval range is reset. This involves an instantaneous increase of PRmad to 80 ms and setting, the PRreset timer to 5. For each R-R interval, if the PRreset timer is >0, the adaptation coefficients X and Y above become 0.5, the constraints on the size of PRmad are removed, and PRreset is decremented. Thus, the expected P-R interval range adapts to a new steady state in 5 beats.

Step 3—Update Beat Code

In a manner similar to the use of beat codes and pattern codes in the various rules of the above-cited Olson et al. a'186 and Gillberg, et al. '736 patents, the specification, the New ST Rule requires that each R-R interval is classified as one of 6 ST beat codes according to the following scheme, in which "paced" indicates that any portion of the R-R interval contained a pacing intervention, excluding safety pacing, and "1:1" signifies that the the R-R interval includes only one or two P-waves and that the RR121 Counter is at least 10. This information, in conjunction with the determinations discussed above with regard to whether the R-R and P-R intervals are as expected is used by the microprocessor to derive a beat code associated with each Current R-R Interval. The following list sets forth the beat code classification system for R-R intervals used by the New ST Rule.

ST Beat code=0 (Paced) and (not 1:1 or R-R interval shorter than expected)

ST Beat code=1 (Paced) and (1:1 and R-R interval as expected)

ST Beat code=2 (Not paced) and (not 1:1 or R-R interval shorter than expected) and (P-R interval as expected)

ST Beat code=3 (Not paced) and (not 1:1 or R-R interval shorter than expected) and (P-R interval not as expected)

ST Beat code=4 (Not Paced) and (1:1 and R-R interval as expected) and (P-R interval as expected)

ST Beat code=5 (Not Paced) and (1:1 and R-R interval as expected) and (P-R not as expected)

When any portion of the R-R interval is paced, the P-R interval cannot be compared to its expected range. Because of the redundancy of the associated recognition machine, discussed below, ST beat codes 1 and 4 and ST beat codes 2 and 3 can theoretically be combined, resulting in only 4 beat codes. However, because the 6 beat codes contain useful information for reviewing episodes, the use of 6 beat codes is recommended.

Step 4—Determine Pattern Codes

Figure 5:
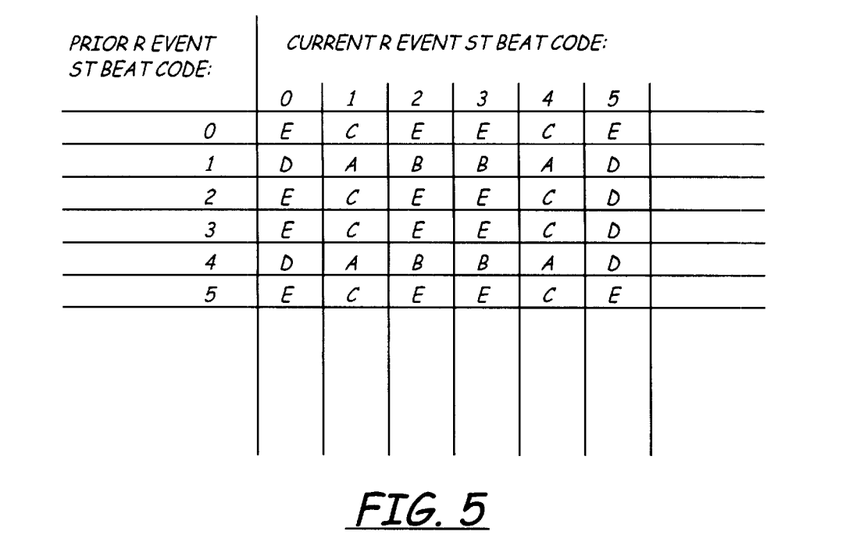
FIG. 5 is a look-up table employed by the New ST Rule to classify pairs of R-R interval beat codes into pattern codes.

Pairs of beat codes are combined by the microprocessor to create ST pattern codes used by the New ST Rule. Because of redundancy, only 5 ST pattern codes are derived: one for normal sinus rhythm, three for ectopy or single beat deviations from the expected 1:1 rhythm, and one to reset the continuous recognition machine for sinus tachycardia recognition, as described below. The look-up table of FIG. 5 is employed by the microprocessor to generate the ST pattern codes. Following each ventricular event, after a determination of the beat code for the Current R-R Interval, the microprocessor derives a new ST pattern code for the Current R-R Interval, according to this table.

Step 5—Update the Continuous Recognition Machine

Figure 6:
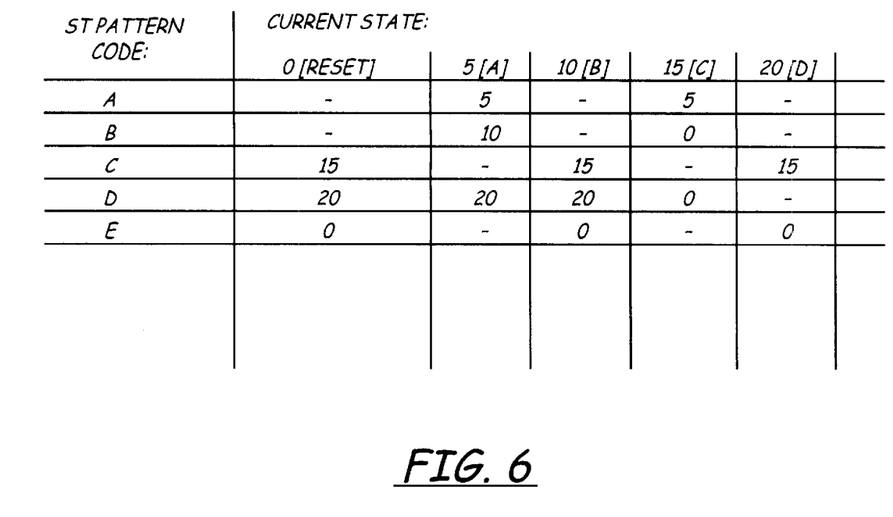
FIG. 6 is a sate machine table employed by the continuous recognition machine of the New ST Rule.

FIG. 6 illustrates the look-up table employed by the New ST Rule in conjunction with a continuous recognition machine for recognizing pattern code sequences corresponding to sinus tachycardia. This type of pattern recognition machine, corresponding generally to those discussed in the Olson, et al. '186 and Gillberg, et al. '736 patents is referred to herein as a continuous recognition machine with exponential decay or "CRMed". The continuous recognition machine is implemented by the microprocessor applying the pattern codes, as they are generated with each ventricular event, to the look-up table. The table defines a set of sequential states, beginning with the reset state 0, and a set of other defined states, arranged horizontally across the table. Possible pattern codes are listed vertically. In operation, with each ventricular event, the processor determines its present state and the most recent pattern code. Based on the table, the processor transitions to the next state, and awaits the next pattern code. As long as the pattern codes adhere to the defined grammar for the rhythm in question, the reset state is avoided. Adherence to the defined grammar over an extended sequence of beats is determined by means of a corresponding count, which may be incremented with each pattern code adhering to the grammar, and may be decremented or reset to zero in response to pattern codes which do not adhere to the grammar as indicated by a return to the reset state. The current count for the continuous recognition machine is compared against a defined threshold value in one clause of the New ST Rules, as discussed below.

The CRMed for the New ST Rule employs a count, "ST Evidence Counter" which is incremented in response to each transition to a non-reset state (or in response to the first R-R interval after a power-on reset or other device reset, where the pattern code is unknown). If the ST Evidence Counter is less than 6, the count is reset to zero on a failure to adhere to the grammar. If the count is 6 or more, a failure to adhere to the grammar causes a decrement of 4, with exponentially increasing decrements of 8, and 16 with each additional, successive failure. For Example, if the count is at 13, three successive failures to meet the grammar will result in clearing of the counter, with shorter sequences of failures to adhere to the grammar causing clearing of the counter at lower counts. On each ventricular event, the ST Evidence Counter is updated by the processor and compared against the threshold values. If the ST Evidence Counter is at least as great as the associated threshold, e.g. 6, the single clause of the New ST Rule is satisfied and the rule remains met until the clause is not satisfied for a defined number of sequential R-R-R intervals. Any rules of lower priority that are met are over-ridden. For example, in the present embodiment as discussed above, the New ST Rule, if met, precludes delivery of therapy in response to any of the VF, FVT or VT rules corresponding to the detection criteria used by the Model 7219 ICD.

When the criterion for tachyarrhythmia episode termination is met, the R-R and P-R expected ranges of the New ST Rule will be placed in reset mode if the ST Evidence Counter is less than the threshold value (nominally 6). Determining the expected R-R and P-R interval ranges in reset mode is accomplished as in conjunction with the initiation of detection. In the rare occasion that the post-treatment rhythm adheres to the existing expected P-R and R-R ranges, the ST Evidence Counter should be 6 or greater at episode termination, and there is no reason to reset the expected ranges.

In the embodiment described above, the adaptive onset mechanism provided by the New ST Rule in which the defined ranges of R-R and P-R intervals vary as a function of both mean interval and interval variability, it should be understood that in some embodiments a simpler adaptive onset mechanism might be employed. For example, RRmad might be a fixed value or a value that varies as a simple function of RRmean. Further, while the above-disclosed embodiment enhances the adaptive onset mechanism provided by ventricular interval information with information related to atrial events, in some embodiments, particularly those in single-chamber ICD's, only ventricular information might be employed. Similarly, in devices employing only atrial sensing, the adaptive onset threshold provided by the New ST Rule might be applied, using A-A intervals instead of R-R intervals as described above. Additionally, while the adaptive onset mechanism of the New ST Rule as described above is implemented using a continuous recognition machine, in some embodiments, alternative mechanisms, such as a simplified counting mechanism might be employed to detect departures of the R-R and/or the P-R intervals from their expected ranges. In general, while the New ST Rule as implemented in the embodiment described above has a multiplicity of features combined to provide a high level of accuracy, individual ones of the features may be modified or deleted in some embodiments of the invention. Similarly, individual features or steps employed by the New ST Rule in the embodiment disclosed above may be useful as stand-alone arrhythmia detection mechanisms and/or in combination with elements of other types of prior art mechanisms.

The above disclosure sets forth a device which requires the use of a microprocessor in order to perform the numerous calculations and analysis steps required. However, it is within the realm of possibility that some or all of the detection criteria provided by the microprocessor in the above disclosure might instead be provided by means of a full custom, integrated circuit, particularly a circuit in which a state counter is employed instead of stored software, in order to control sequential operation of the digital circuitry, along the general lines of the circuits disclosed in U.S. Pat. No. 5,088,488, issued to Markowitz et al. and U.S. Pat. No. 5,052,388, issued to Sivula et al., both of which are incorporated herein by reference in their entireties. Thus, the above description should be considered exemplary, rather than limiting, with regard to the interpretation of the following claims.

I claim:

1. A method of identifying sinus rhythm in a patient's heart, comprising:
   measuring intervals between depolarizations of a single chamber of a patient's heart;
   deriving an average value based upon preceding measured intervals between depolarizations of the single chamber;
   determining a variability value based upon preceding measured intervals between depolarizations of the single chamber;
   defining a first expected range of future measured intervals between depolarizations of the single chamber based upon the average value and the variability value; and
   responsive to future measured intervals between depolarizations of the single chamber falling within the first expected range, determining that the patient is in a sinus rhythm.

2. The method of claim 1 wherein deriving the average value comprises deriving a mean value of preceding intervals between depolarizations of the single chamber.

3. The method of claim 2 wherein deriving the mean value comprises deriving a trimmed mean value of preceding intervals between depolarizations of the single chamber.

4. The method of claim 1 or claim 2 or claim 3 above, wherein measuring intervals between depolarizations of the single chamber comprises measuring intervals between depolarizations of a ventricle of the patient's heart.

5. The method of claim 4, further comprising:
   measuring intervals between depolarizations of two chambers of the patient's heart;
   defining a second expected range of future measured intervals between depolarizations of the two chambers; and
   responsive to future measured intervals between depolarizations of the two chambers falling within the second expected range, determining that the patient is in a sinus rhythm.

6. The method of claim 4, further comprising:
   determining whether the patient's heart is in a 1:1 rhythm; and
   responsive to a determination that the patient's heart is in a 1:1 rhythm, determining that the patient is in a sinus rhythm.

7. The method of claim 1, further comprising:
   measuring intervals between depolarizations of two chambers of the patient's heart;
   defining a second expected range of future measured intervals between depolarizations of the two chambers; and
   responsive to future measured intervals between depolarizations of the two chambers falling within the second expected range, determining that the patient is in a sinus rhythm.

8. The method of claim 1, further comprising:
   determining whether the patient's heart is in a 1:1 rhythm; and
   responsive to a determination that the patient's heart is in a 1:1 rhythm, determining that the patient is in a sinus rhythm.

9. A method of identifying sinus rhythm in a patient's heart, comprising:
   measuring intervals between depolarizations of a single chamber of a patient's heart;
   based upon the measured intervals, defining a first expected range of future measured intervals between depolarizations of the single chamber;
   determining whether the patient is in a 1:1 rhythm; and
   responsive to future measured intervals between depolarizations of the single chamber falling within the first expected range while the patient is in a 1:1 rhythm, determining that the patient is in a sinus rhythm.

10. The method of claim 9 wherein defining the first expected range comprises deriving an average value of preceding intervals between depolarizations of the single chamber and defining the first expected range based upon the average value.

11. The method of claim 10 wherein deriving the average value comprises deriving a mean value of preceding intervals between depolarizations of the single chamber.

12. The method of claim 10 or claim 11, wherein defining the first expected range further comprises deriving a value of the variability of preceding measured intervals between depolarizations of the single chamber and defining the first expected range based upon the average value and the variability value.

13. The method of claim 9 or claim 10 or claim 11, wherein measuring intervals between depolarizations of the single chamber comprises measuring intervals between depolarizations of a ventricle of the patient's heart.

14. The method of claim 13, further comprising:
  measuring intervals between two chambers of the patient's heart;
  defining a second expected range of future measured intervals between depolarizations of the two chambers; and
  responsive to future measured intervals between depolarizations of the two chambers falling within the second expected range, determining that the patient is in a sinus rhythm.

15. The method of claim 9, further comprising:
  measuring intervals between two chambers of the patient's heart;
  defining a second expected range of future measured intervals between depolarizations of the two chambers; and
  responsive to future measured intervals between depolarizations of the two chambers falling within the second expected range, determining that the patient is in a sinus rhythm.

16. A method of identifying sinus rhythm in a patient's heart, comprising:
  measuring intervals between depolarizations of a single chamber of a patient's heart;
  measuring intervals between two chambers of the patient's heart;
  defining a first expected range of future measured intervals between depolarizations of the single chamber of a patient's heart;
  defining a second expected range of future measured intervals between depolarizations of the two chambers of the patient's heart; and
  responsive to future measured intervals between depolarizations of the single chamber of a patient's heart falling within the first expected range and to future measured intervals between depolarizations of the two chambers of the patient's heart falling within the second expected range, determining that the patient is in a sinus rhythm.

17. The method of claim 16 wherein defining the first expected range comprises deriving an average value of preceding intervals between depolarizations of the single chamber and defining the first expected range based upon the average value.

18. The method of claim 17 wherein deriving the average value comprises deriving a mean value of preceding intervals between depolarizations of the single chamber.

19. The method of claim 17 or claim 18, wherein defining the first expected range further comprises deriving a value of the variability of preceding measured intervals between depolarizations of the single chamber and defining the first expected range based upon the average value and the variability value.

20. The method of claim 16 or claim 17 or claim 18, wherein measuring intervals between depolarizations of the single chamber of the patient's heart comprises measuring intervals between depolarizations of a ventricle of the patient's heart.

21. The method of claim 16 wherein defining the second expected range comprises deriving an average value of preceding intervals between depolarizations of the two chambers and defining the second expected range based upon the average value.

22. The method of claim 21 wherein deriving the average value comprises deriving a mean value of preceding intervals between depolarizations of the two chambers.

23. The method of claim 21 or claim 22, wherein defining the second expected range further comprises deriving a value of the variability of preceding measured intervals between depolarizations of the two chambers and defining the second expected range based upon the average value and the variability value.

24. The method of claim 16 or claim 21 or claim 22, wherein measuring intervals between depolarizations of the two chambers comprises measuring intervals between depolarizations of an atrium and a ventricle of the patient's heart.

25. The method of claim 16, further comprising:
  determining whether the patient's heart is in a 1:1 rhythm; and
  responsive to a determination that the patient's heart is in a 1:1 rhythm, determining that the patient is in a sinus rhythm.

26. An apparatus for identifying sinus rhythm in a patient's heart, comprising:
  means for measuring intervals between depolarizations of a single chamber of a patient's heart;
  means for deriving an average value based upon preceding measured intervals between depolarizations of the single chamber;
  means for determining a variability value based upon preceding measured intervals between depolarizations of the single chamber;
  means for defining a first expected range of future measured intervals between depolarizations of the single chamber based upon the average value and the variability value; and
  means responsive to future measured intervals between depolarizations of the single chamber falling within the first expected range, for determining that the patient is in a sinus rhythm.

27. The apparatus of claim 26 wherein the means for deriving the average value comprises means for deriving a mean value of preceding intervals between depolarizations of the single chamber.

28. The apparatus of claim 27 wherein deriving the mean value comprises deriving a trimmed mean value of preceding intervals between depolarizations of the single chamber.

29. The apparatus of claim 26 or claim 27 or claim 28 above, wherein the means for measuring intervals between depolarizations of the single chamber comprises means for measuring intervals between depolarizations of a ventricle of the patient's heart.

30. The apparatus of claim 29, further comprising:
  means for measuring intervals between depolarizations of two chambers of the patient's heart;

means for defining a second expected range of future measured intervals between depolarizations of the two chambers; and means responsive to future measured intervals between depolarizations of the two chambers falling within the second expected range, for determining that the patient is in a sinus rhythm.

31. The apparatus of claim 30, further comprising:

means for determining whether the patient's heart is in a 1:1 rhythm; and means responsive to a determination that the patient's heart is in a 1:1 rhythm, for determining that the patient is in a sinus rhythm.

32. The apparatus of claim 26, further comprising:

means for measuring intervals between depolarizations of two chambers of the patient's heart;

means for defining a second expected range of future measured intervals between depolarizations of the two chambers; and means responsive to future measured intervals between depolarizations of the two chambers falling within the second expected range, for determining that the patient is in a sinus rhythm.

33. The apparatus of claim 26, further comprising:

means for determining whether the patient's heart is in a 1:1 rhythm; and means responsive to a determination that the patient's heart is in a 1:1 rhythm, for determining that the patient is in a sinus rhythm.

34. An apparatus for identifying sinus rhythm in a patient's heart, comprising:

means for measuring intervals between depolarizations of a single chamber of a patient's heart;

means for defining a first expected range of future measured intervals between depolarizations of the single chamber, based upon the measured intervals between depolarizations of the single chamber;

means for determining whether the patient is in a 1:1 rhythm; and means responsive to future measured intervals between depolarizations of the single chamber falling within the first expected range while the patient is in a 1:1 rhythm, for determining that the patient is in a sinus rhythm.

35. The apparatus of claim 34 wherein the means for defining the first expected range comprises means for deriving an average value of preceding intervals between depolarizations of the single chamber and means for defining the first expected range based upon the average value.

36. The apparatus of claim 35 wherein the means for deriving the average value comprises means for deriving a mean value of preceding intervals between depolarizations of the single chamber.

37. The apparatus of claim 35 or claim 36, wherein the means for defining the first expected range further comprises means for deriving a value of the variability of preceding measured intervals between depolarizations of the single chamber and means for defining the first expected range based upon the average value and the variability value.

38. The apparatus of claim 34 or claim 35 or claim 36, wherein the means for measuring intervals between depolarizations of the single chamber comprises means for measuring intervals between depolarizations of a ventricle of the patient's heart.

39. The apparatus of claim 38, further comprising:

means for measuring intervals between two chambers of the patient's heart;

means for defining a second expected range of future measured intervals between depolarizations of the two chambers; and means responsive to future measured intervals between depolarizations of the two chambers of the patient's heart falling within the second expected range, for determining that the patient is in a sinus rhythm.

40. The apparatus of claim 34, further comprising:

means for measuring intervals between two chambers of the patient's heart;

means for defining a second expected range of future measured intervals between depolarizations of the two chambers; and means responsive to future measured intervals between depolarizations of the two chambers of the patient's heart falling within the second expected range, for determining that the patient is in a sinus rhythm.

41. An apparatus for identifying sinus rhythm in a patient's heart, comprising:

means for measuring intervals between depolarizations of a single chamber of a patient's heart;

means for measuring intervals between two chambers of the patient's heart;

means for defining a first expected range of future measured intervals between depolarizations of the single chamber of a patient's heart;

means for defining a second expected range of future measured intervals between depolarizations of the two chambers of the patient's heart; and means responsive to future measured intervals between depolarizations of the single chamber of a patient's heart falling within the first expected range and to future measured intervals between depolarizations of the two chambers of the patient's heart falling within the second expected range, for determining that the patient is in a sinus rhythm.

42. The apparatus of claim 41 wherein the means for defining the first expected range comprises means for deriving an average value of preceding intervals between depolarizations of the single chamber and means for defining the first expected range based upon the average value.

43. The apparatus of claim 42 wherein the means for deriving the average value comprises means for deriving a mean value of preceding intervals between depolarizations of the single chamber.

44. The apparatus of claim 42 or claim 43, wherein the means for defining the first expected range further comprises deriving a value of the variability of preceding measured intervals and means for defining the first expected range based upon the average value and the variability value.

45. The apparatus of claim 41 or claim 42 or claim 43, wherein the means for measuring intervals between depolarizations of the single chamber of the patient's heart comprises means for measuring intervals between depolarizations of a ventricle of the patient's heart.

46. The apparatus of claim 41 wherein the means for defining the second expected range comprises means for deriving an average value of preceding intervals between depolarizations of the two chambers and defining the second expected range based upon the average value.

47. The apparatus of claim 46 wherein the means for deriving the average value comprises means for deriving a mean value of preceding intervals between depolarizations of the two chambers.

48. The apparatus of claim 46 or claim 47, wherein the means for defining the second expected range further comprises means for deriving a value of the variability of preceding measured intervals and means for defining the second expected range based upon the average value and the variability value.

49. The apparatus of claim 41 or claim 46 or claim 47, wherein the means for measuring intervals between depolarizations of the two chambers comprises means for measuring intervals between depolarizations of an atrium and a ventricle of the patient's heart.

50. The apparatus of claim 41, further comprising:

means for determining whether the patient's heart is in a 1:1 rhythm; and means responsive to a determination that the patient's heart is in a 1:1 rhythm, for determining that the patient is in a sinus rhythm.

\* \* \* \* \*